United States Patent
Lorenzo et al.

(10) Patent No.: US 11,123,077 B2
(45) Date of Patent: Sep. 21, 2021

(54) INTRASACCULAR DEVICE POSITIONING AND DEPLOYMENT SYSTEM

(71) Applicant: DePuy Synthes Products, Inc., Raynham, MA (US)

(72) Inventors: Juan Lorenzo, Raynham, MA (US); Kirk Johnson, Raynham, MA (US); Lacey Gorochow, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 108 days.

(21) Appl. No.: 16/140,836

(22) Filed: Sep. 25, 2018

(65) Prior Publication Data

US 2020/0093499 A1 Mar. 26, 2020

(51) Int. Cl.
*A61B 17/12* (2006.01)
*A61B 17/00* (2006.01)

(52) U.S. Cl.
CPC .. *A61B 17/12113* (2013.01); *A61B 17/12031* (2013.01); *A61B 17/12172* (2013.01);
(Continued)

(58) Field of Classification Search
CPC ........ A61B 17/12113; A61B 17/12022; A61B 17/12031; A61B 17/12109; A61B 17/12172; A61B 17/1214; A61B 17/12145; A61B 17/12168; A61B 17/12027; A61B 17/2036; A61B 17/1204; A61B 2017/1205; A61B 2017/12054; A61F 2/95; A61F 2/9522; A61F 2/962; A61F 2/966;
(Continued)

(56) References Cited

U.S. PATENT DOCUMENTS 2,849,002 A 8/1958 Oddo
3,480,017 A 11/1969 Shute
(Continued)

FOREIGN PATENT DOCUMENTS

CA 2395796 A1 7/2001
CA 2 431 594 A1 9/2002
(Continued)

OTHER PUBLICATIONS

Extended European Search Report issued in European Patent Application No. 19 19 9204 dated Jan. 21, 2020.
(Continued)

*Primary Examiner* — Melanie R Tyson
*Assistant Examiner* — Uyen N Vo
(74) *Attorney, Agent, or Firm* — Troutman Pepper Hamilton Sanders LLP (57) ABSTRACT

Implant deployment systems can generally can include a braided implant that can be detachably attached to a delivery tube by an expansion ring that can be positioned within a notch on an outer surface of the delivery tube near a distal end of the delivery tube. The implant can be positioned within a lumen of the delivery tube and remain attached to the delivery tube as the assembly is fed through a microcatheter to a treatment site. Once the braided implant is implanted, the expansion ring can move from a collapsed configuration that is engaged with the notch of the delivery tube to a deployed configuration that releases the delivery tube, thereby releasing the braided implant from the delivery tube.

14 Claims, 9 Drawing Sheets

(52) U.S. Cl.
CPC ............... *A61B 2017/00867* (2013.01); *A61B 2017/12054* (2013.01)

(58) Field of Classification Search
CPC ...... A61F 2002/9505; A61F 2002/9528; A61F 2002/9534; A61F 2002/954; A61F 2002/9665

See application file for complete search history.

(56) References Cited

U.S. PATENT DOCUMENTS

| | | | |
|---|---|---|---|
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,916,235 A | 6/1999 | Guglielmi |
| 5,891,128 A | 7/1999 | Chin et al. |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,777,974 B2 | 8/2004 | Eichfeld et al. |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,974,512 B2 | 12/2005 | Henry et al. |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Feoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Fran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | Burg et al. |
| 8,523,902 B2 | 9/2013 | Heaven et al. |
| 8,551,132 B2 | 10/2013 | Eskridge et al. |
| 8,900,304 B1 | 12/2014 | Mobaid |
| 8,992,568 B2 | 3/2015 | Duggal et al. |
| 8,998,947 B2 | 3/2015 | Aboytes et al. |
| 9,055,948 B2 | 6/2015 | Jaeger et al. |
| 9,107,670 B2 | 8/2015 | Hannes |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |

(56) References Cited

U.S. PATENT DOCUMENTS

| | | |
|---|---|---|
| 9,539,122 B2 | 1/2017 | Bowman |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Bumes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign |
| 9,681,861 B2 | 6/2017 | Heisei et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman |
| 9,833,252 B2 | 12/2017 | Sepetka |
| 9,833,604 B2 | 12/2017 | Lam |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisei et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,716,573 B2 | 7/2020 | Connor |
| 2001/0044595 A1 | 11/2001 | Reydel et al. |
| 2002/0068974 A1 | 6/2002 | Kuslich et al. |
| 2002/0082638 A1 | 6/2002 | Porter et al. |
| 2002/0143349 A1* | 10/2002 | Gifford, III ........ A61B 17/12109 606/157 |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Tassel et al. |
| 2003/0171739 A1* | 9/2003 | Murphy ........... A61B 17/12168 606/1 |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Gutterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1* | 6/2011 | Marchand ........ A61B 17/12172 623/1.2 |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Muller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |

(56) References Cited

U.S. PATENT DOCUMENTS

| | | |
|---|---|---|
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2014/0277096 A1 | 9/2014 | Richter et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1* | 9/2016 | Hewitt ............ A61B 17/12177 606/200 |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero |
| 2017/0079680 A1 | 3/2017 | Bowman |
| 2017/0079717 A1 | 3/2017 | Walsh et al. |
| 2017/0079766 A1 | 3/2017 | Wang |
| 2017/0079767 A1 | 3/2017 | Leon-Yip |
| 2017/0079812 A1 | 3/2017 | Lam et al. |
| 2017/0079817 A1 | 3/2017 | Sepetka |
| 2017/0079819 A1 | 3/2017 | Pung et al. |
| 2017/0079820 A1 | 3/2017 | Lam et al. |
| 2017/0086851 A1 | 3/2017 | Wallace |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Laizzo |
| 2017/0113023 A1 | 4/2017 | Steingisser et al. |
| 2017/0114350 A1 | 4/2017 | Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1* | 8/2017 | Bowman ................ B29C 71/02 |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh |
| 2017/0303942 A1 | 10/2017 | Greenhalgh et al. |
| 2017/0303947 A1 | 10/2017 | Greenhalgh |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman |
| 2017/0333228 A1 | 11/2017 | Orth et al. |
| 2017/0333236 A1 | 11/2017 | Greenan |
| 2017/0333678 A1 | 11/2017 | Bowman |
| 2017/0340333 A1 | 11/2017 | Badruddin et al. |
| 2017/0340383 A1 | 11/2017 | Bloom et al. |
| 2017/0348014 A1 | 12/2017 | Wallace |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0069313 A1 | 3/2020 | Ku et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 102013106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |

(56) References Cited

FOREIGN PATENT DOCUMENTS

| | | |
|---|---|---|
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | WO 2005117718 A1 | 12/2005 |
| WO | WO 2006034149 A2 | 3/2006 |
| WO | WO 2006052322 A2 | 5/2006 |
| WO | WO 2007076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | WO 2015160721 A1 | 10/2015 |
| WO | WO 2015166013 A1 | 11/2015 |
| WO | WO 2015171268 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | 2012/034135 A1 | 3/2021 |

OTHER PUBLICATIONS

Aites et al. Creation of Saccular Aneurysms in the Rabbit: A Model Suitable for Testing Endovascular Devices AJR 2000; 174: 349-354.
Schaffer, Advanced Materials & Processes, Oct. 2002, pp. 51-54.

* cited by examiner

INTRASACCULAR DEVICE POSITIONING AND DEPLOYMENT SYSTEM

FIELD OF INVENTION

The present invention generally relates to medical instruments, and more particularly, delivery systems for a device for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include occlusion devices that either fill the sac of the aneurysm with embolic material or treating the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current occlusion devices typically utilize multiple embolic coils to either fill the sac or treat the entrance. In either treatment, obtaining an embolic coil packing density sufficient to either occlude the aneurysm neck or fill the aneurysm sac is difficult and time consuming. Further, aneurysm morphology (e.g. wide neck, bifurcation, etc.) can required ancillary devices such a stents or balloons to support the coil mass and obtain the desired packing density.

Naturally formed thrombotic masses formed by treating the entrance of the aneurysm with embolic coils can improve healing compared to aneurysm masses packed with embolic coils by reducing possible distention from arterial walls and permitting reintegration into the original parent vessel shape along the neck plane. However, embolic coils delivered to the neck of the aneurysm can potentially have the adverse effect of impeding the flow of blood in the adjoining blood vessel; at the same time, if the entrance is insufficiently packed, blood flow can persist into the aneurysm. Properly implanting embolic coils is therefore challenging, and once implanted, the coils cannot easily be retracted or repositioned.

Furthermore, embolic coils do not always effectively treat aneurysms as aneurysms treated with multiple coils often reanalyze or compact because of poor coiling, lack of coverage across the aneurysm neck, because of flow, or even aneurysm size.

An example alternative occlusion device is described in U.S. Pat. No. 8,998,947. However, this approach relies upon the use of embolic coils or mimics the coil approach and therefore suffers many of the limitations of embolic coil approaches such as difficulty achieving a safe packing density and inability to reposition once implanted.

It is therefore desirable to have a device which easily, accurately, and safely occludes a neck of an aneurysm or other arterio-venous malformation in a parent vessel without blocking flow into perforator vessels communicating with the parent vessel.

SUMMARY

Disclosed herein are various exemplary devices and systems of the present invention that can address the above needs. The devices generally can include a braided implant that can be detachably attached to a delivery tube by an expansion ring that can be positioned within a notch on an outer surface of the delivery tube near a distal end of the delivery tube. The implant can be positioned within a lumen of the delivery tube and remain attached to the delivery tube as the delivery tube and implant device assembly is fed through a microcatheter to a treatment site. Once at the treatment site, the braided implant can be implanted by pushing an inner elongated member, or pusher distally, thereby pushing the braided implant out of the distal end of the delivery tube. The inner elongated member can be detachably attached to an end of the braided implant such that the braided implant can be retracted and repositioned until properly positioned, then released. Once the braided implant is implanted, the expansion ring can move from a collapsed configuration that is engaged with the notch of the delivery tube to a deployed configuration that releases the delivery tube. Once released, the delivery tube can be extracted from the patient, leaving behind the implanted braided implant.

An example system for releasing an implant can include a braided implant, a delivery tube, an inner elongated member, and an expansion ring. The braided implant can have a first end detachably attached to a distal end of the inner elongated member and a second end mechanically connected to the expansion ring. The delivery tube can have a distal end with a notch positioned on an outer surface near the distal end of the delivery tube. The expansion ring can be movable from a collapsed configuration that is engaged with the notch to a deployed configuration that is disengaged from the notch and released from the delivery tube.

The braided implant can include a fold positioned distal the distal end of the delivery tube, an outer fold segment extending proximally from the fold, and an inner fold segment extending proximally from the fold such that the outer fold segment encompasses the inner fold segment. The outer fold segment can include the second end of the braided implant attached to the expansion ring, and the inner fold segment can include the first end attached to the inner elongated member.

The delivery tube can have a lumen therethrough and the inner fold segment of the braided implant can be positioned within the lumen.

The expansion ring can be mechanically connected to a portion of the outer fold segment such that the outer fold segment covers at least a portion of the notch and at least a portion of the expansion ring.

In the deployed configuration, the expansion ring can include an attached segment and an extending portion. The attached segment can be attached to the braided implant and can open a first region of the occlusive sack to a first circumference, and the extending portion can be attached to the attaching segment and can open a second region of the occlusive sack to a second circumference greater than the first circumference.

The expansion ring can have leaf shaped elements that extend radially as the expansion ring moves from the collapsed configuration to the deployed configuration.

The expansion ring can have segments joined to form a substantially tubular zig-zag structure when in the collapsed configuration.

The inner elongated member can be pushed distally to implant at least a portion of the braided implant.

An example device for treating an aneurysm can include a tubular delivery member, an inner elongated member, a braided tubular implant, and an expansion component. The braided tubular implant can be movable from a delivery configuration to an implanted configuration. In the delivery configuration, the braided tubular implant can have a first end extending proximally within an interior of the tubular delivery member that is detachably attached to a distal end of the inner elongated member and a second end extending distally from the distal end of the tubular delivery member and folding proximally over at least a portion of a notch positioned on an exterior of the tubular delivery member near a distal end of the tubular delivery member. The expansion component can be positioned within the notch on the tubular delivery member and attached to the braided tubular implant near the second end of the braided tubular implant. The expansion component can be movable from a collapsed configuration engaging the notch to a deployed configuration disengaging the notch.

The notch on the exterior of the tubular delivery member can be a circumferential indentation. The expansion component can be positioned in the circumferential indentation when in the collapsed configuration.

When in the implanted configuration, the braided tubular implant can have an occlusive sack and the expansion component can be positioned within the occlusive sack. The expansion component can have extending members that appose the occlusive sack when the expansion component is in the deployed configuration. When in the collapsed configuration, the expansion component can have an opening through which the braided tubular implant passes through upon movement from the delivery configuration to the implanted configuration.

An example method for treating an aneurysm can include the steps of providing a braided implantation delivery system having a braided implant, a delivery tube, and an expansion component, attaching the braided implant to the expansion component, engaging the expansion component with a notch on the delivery tube, implanting the braided implant in the aneurysm, expanding the expansion component to disengage the expansion component from the notch, and releasing the expansion component from the delivery tube which releases the braided implant from the delivery tube.

The method can further include the step of expanding the expansion component to occlude at least a portion of the neck of the aneurysm.

The step of implanting the braided implant in the aneurysm can include the step of forming an occlusive sack, and the step of expanding the expansion component can include the step of extending the occlusive sack across the neck of the aneurysm.

The provided braided implantation delivery system can further include an inner elongated member, and the method can further include the step of attaching the braided implant to the inner elongated member. The step of implanting the braided implant can further include the steps of pushing the inner elongated member distally, thereby pushing a portion of the braided implant into the aneurysm and detaching the braided implant from the inner elongated member.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

Previous approaches utilizing embolic coils can be improved upon by treating the aneurysm entrance and/or packing the aneurysm with an embolic braided implant. For example, see U.S. patent application Ser. No. 15/903,860, which has been Published as US 2018/0242979 A1 on Aug. 30, 2018 and patented as U.S. Pat. No. 10,751,066 B2 on Aug. 25, 2020, incorporated herein, in its entirety, by reference. Treating the aneurysm with the braided implant can have potential advantages over treatments utilizing embolic coils such as an ability to achieve higher packing density, ability to retract and reposition the implant during the implantation procedure, ability to perform implantation without ancillary devices such as stents or balloons, reduced risk of reanalyzing or compacting, and improved coverage across the aneurysm neck, for example.

In braided implant delivery systems, it can be advantageous to maintain an attachment between an implant and a delivery device until the implant is in place at the treatment site, then detach the implant so that portions of the delivery device and system can be extracted. When implanted in an aneurysm, for example, the delivery system can also serve to at least partially occlude the neck of the aneurysm. The present disclosure describes various example systems, devices, and methods that can be utilized for at least such purposes.

The system for positioning and deployment of an intrasaccular device (e.g. braided implant) into an aneurysm can include an outer hollow braid pusher, an inner braid pusher, a braided implant, and a microcatheter. The outer pusher (delivery tube) be coaxially mounted over the inner pusher (inner elongated member). A first (proximal) end of the braided implant (braided intrasaccular component) can be mounted to a distal end of the outer pusher, while a second (distal) end of the braided implant can be attached to a distal end of the inner pusher. The first end of the braided implant can have a self-expanding ring mounted to the braid. The self-expanding ring can be made of Nitinol or other similar self-expanding material. The self-expanding ring can be crimped in place within a notch located at a distal end of the outer pusher to attach the braided implant to the outer pusher, and the first, proximal end of the braided implant can fit within a notch at the distal end of the inner pusher. The inner pusher can include a release mechanism of known design. For example, see U.S. Pat. Nos. 7,377,932 and 8,062,325, each incorporated herein, in their entirety, by reference.

Figure 1:
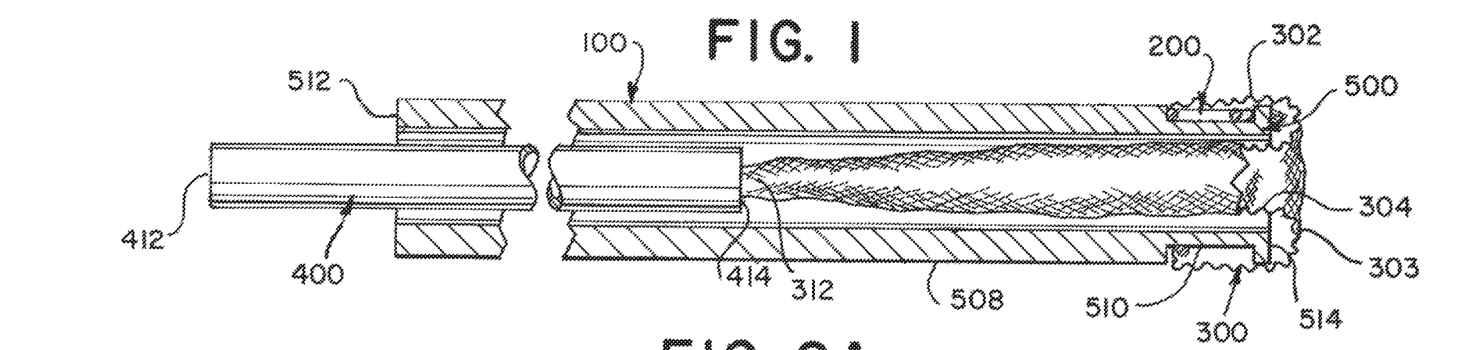
FIG. 1 is a cross-sectional drawing of an implantation device or system according to the present invention.

FIG. 1 depicts a cross-sectional view of an implantation device 100 having a braided implant 300, a delivery tube 500, and an inner elongated member 400. The braided implant 300 can have an outer fold segment 302 near a distal end 314 of the braided implant 300. The outer fold segment 302 can be attached to an expansion ring 200, and the expansion ring 200 can be positioned within a notch 510 on an outer surface 508 of the delivery tube 500 near a distal end 514 of the delivery tube 500. The braided implant can have a fold 303 positioned distal the distal end 514 of the delivery tube 500 such that the outer fold segment 302 extends proximally from the fold 303 over the delivery tube 500 and an inner fold segment 304 extends proximally from the fold 303 within the delivery tube 500. The inner fold segment 304 can extend to a proximal end 312 of the braided implant 300, and a distal end 414 of the inner elongated member 400 can be detachably attached to the proximal end 312 of the braided implant 300. The delivery tube 500 and the inner elongated member 400 can each have proximal ends 512, 412 that can be accessible by a user for manipulation of the device 100 during treatment.

Figures 2A, 2B, 2C:
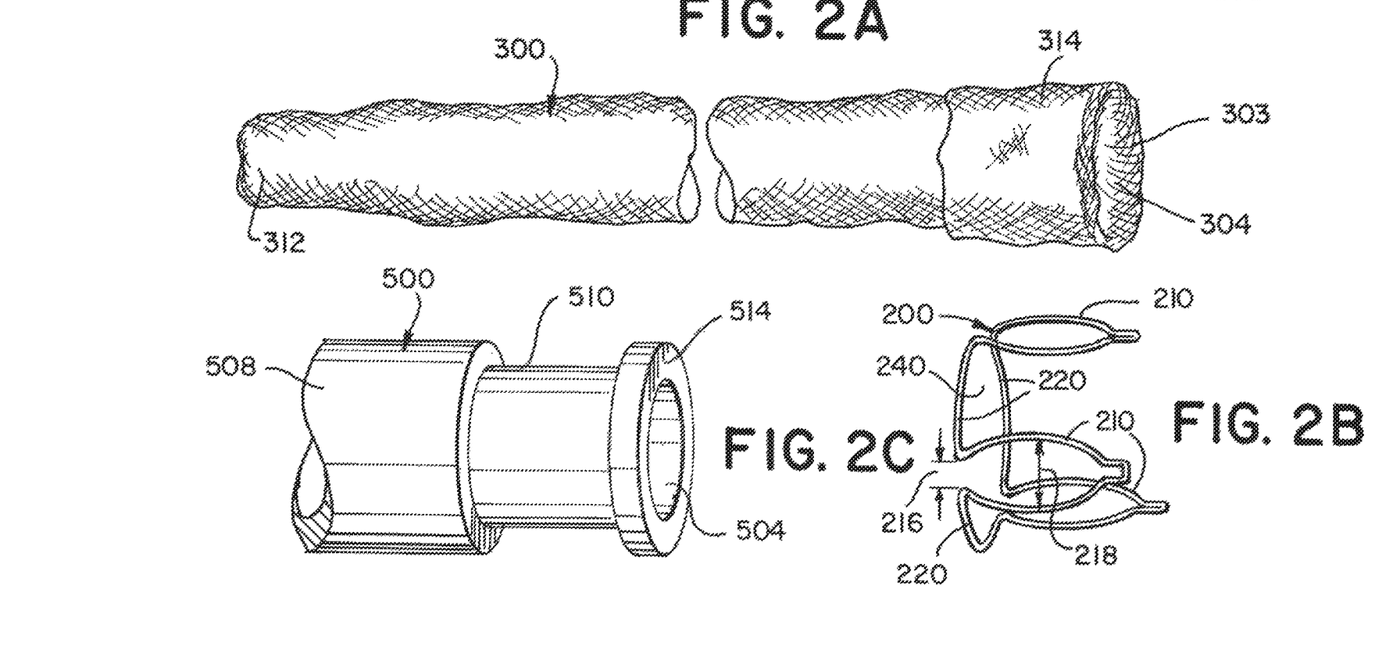
FIG. 2A is a drawing depicting braided implant in a delivery configuration according to the present invention.
FIG. 2B is a drawing depicting an expansion ring in a collapsed configuration according to the present invention.
FIG. 2C is a drawing depicting a distal end of a delivery tube according to the present invention.

FIGS. 2A to 2C depict a braided implant 300, an expansion ring 200, and a delivery tube 500 that can be assembled to form at least part of an implantation device, such as the device 100 depicted in FIG. 1. FIG. 2A depicts the braided implant 300 in a delivery configuration having an outer fold segment 302 separated from an inner fold segment 304 by a fold 303. The inner fold 304 can be sized to fit within a lumen 504 of the delivery tube 504 such as the delivery tube 500 depicted in FIG. 2C. The inner fold 304 can extend to a first end 312 that can attach to an inner elongated member (not shown). The outer fold segment 302 can be positioned at a second end 314 of the braided implant and can be sized to fit over an expansion ring 200, such as the expansion ring 200 depicted in FIG. 2B. The outer fold segment 302 can also be sized to fit over a distal end 514 of a delivery tube 500 such as the delivery tube depicted in FIG. 2C.

FIG. 2B depicts the expansion ring 200 in a collapsed configuration. In the collapsed configuration, the expansion ring 200 can be sized to fit within a notch 510 on an outer surface 508 of a delivery tube 500 such as the delivery tube 500 depicted in FIG. 2C. The expansion ring 200 can include extending portions 210 that are attached by attaching segments 220 to form a ring having an opening 240 sized to fit within the delivery tube notch 510. Each extending portion 210 can have a petal or oval shape such as shown in FIG. 2B, and the shape can be characterized by a first width 216 at a base of the extending portion 210 and a second width 218 near a middle of the extending portion that is wider than the first width 216.

FIG. 2C depicts a portion of a delivery tube 500 near a distal end 514 of the delivery tube 500. As discussed in reference to FIGS. 2A and 2B, the delivery tube 500 can have notch 510 near its distal end 514 on its outer surface 508, and the delivery tube 500 can have a lumen 504 therethrough.

Figure 3:
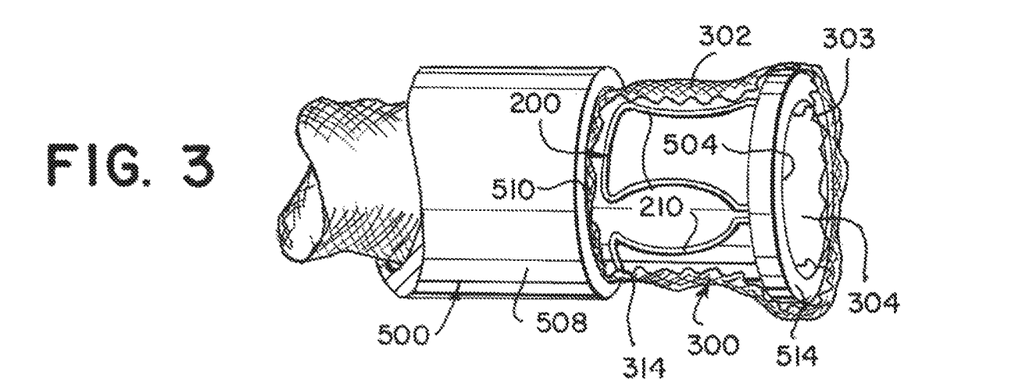
FIG. 3 is a drawing depicting a distal end of an implantation system according to the present invention.

FIG. 3 depicts a braided implant 300, expansion ring 200, and delivery tube 500 such as those depicted in FIGS. 2A to 2C assembled together to form an implantation device. As shown, an outer fold segment 302 of the braided implant 300 can be folded over and attached to an expansion ring 200, and the expansion ring 200 can be sized to fit within a notch 510 on an outer surface 508 of the delivery tube 500. An inner fold segment 304 of the braided implant 300 can extend into a lumen 504 of the delivery tube. Configured thusly, the depicted device can be inserted into a microcatheter for delivery to a treatment site.

Figure 4:
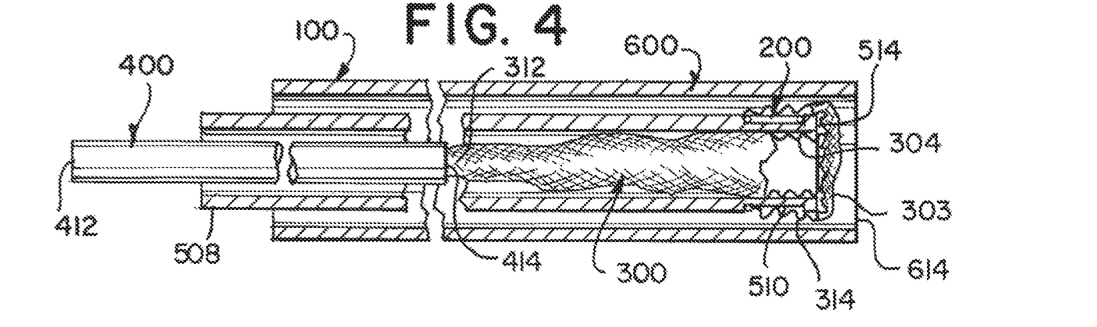
FIG. 4 is a cross-sectional drawing of an implantation system within a microcatheter according to the present invention.

FIG. 4 depicts a cross-sectional view of an implantation system including a device 100 positioned within a microcatheter 600 for delivery to a treatment site. The microcatheter can be any catheter suitable for insertion into a patient and navigation to a treatment site. Once in place, the implantation device 100 can be fed through the catheter 600 to the treatment site. The catheter 600 can have a distal end 614 that can be positioned at a treatment site and a proximal end 612 that can be accessible to a user during a treatment procedure.

Figure 5A:
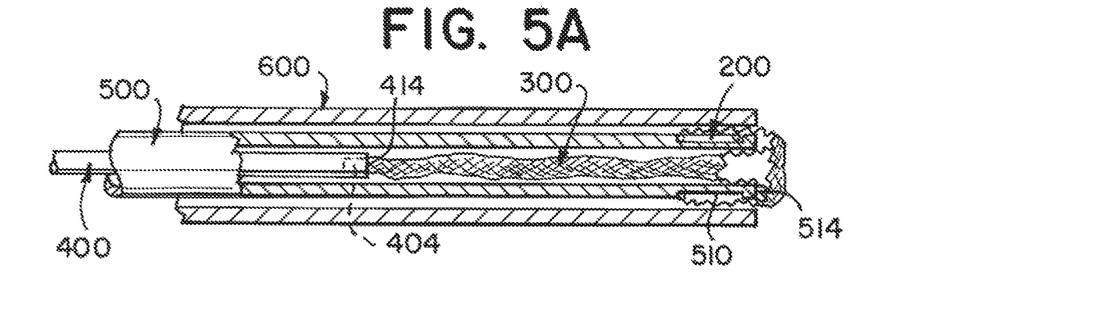
FIGS. 5A to 5G are drawings illustrating a method of use of an implantation system according to the present invention.

FIGS. 5A to 5G are cross-sectional drawings illustrating a method of use of an implantation system for treatment of an aneurysm. FIG. 5A depicts an implantation system configured to begin implantation of the braided implant. As shown, the device can be approximately aligned with a distal end 614 of the microcatheter 600. The braided implant 300 can be attached to an expansion ring 200 within a delivery tube notch 510 and can extend within the delivery tube 500 to attach to an inner elongated member 400 at a braid release 400.

Figure 5B:
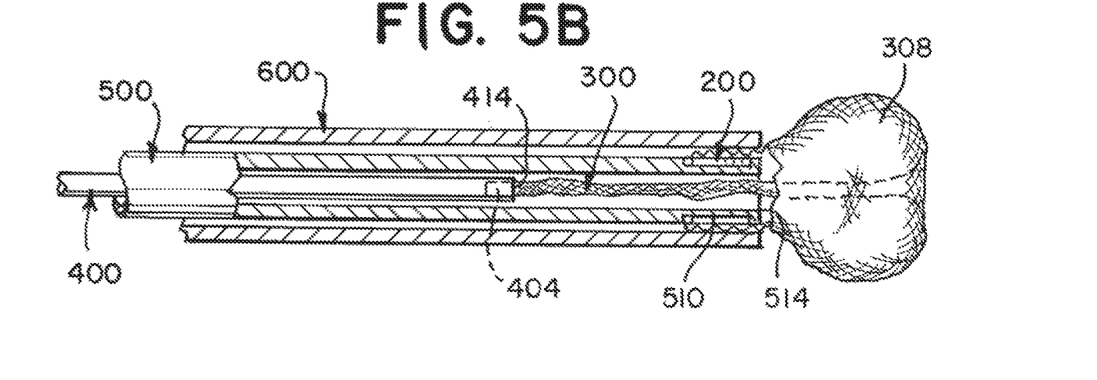

FIG. 5B depicts a partially implanted braided implant 300. As shown, the inner elongated member 400 can be pushed distally, pushing the braided implant 300 out of the delivery tube 500 and microcatheter 600. As the braided implant 300 exits the delivery tube 500, the implant 300 can invert and begin to form an occlusive sack 308.

Figure 5C:
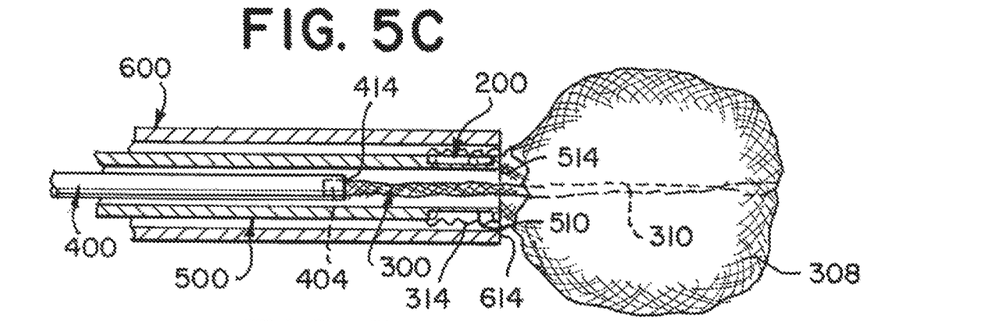

As shown in FIG. 5C, the inner elongated member 400 can be continued to be pushed distally, pushing more of the braided implant 300 out of the delivery tube 500. As the braided implant 300 further exits the delivery tube 500, the implant 300 can continue to invert and the occlusive sack 308 can expand.

Figure 5D:
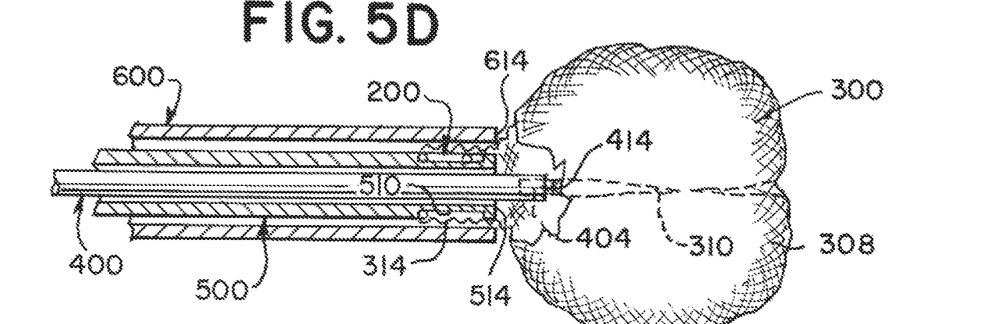

As shown in FIG. 5D, the inner elongated member 400 can be pushed until the braided implant 300 fully exits the delivery tube. As shown, the occlusive sack 308 can be fully expanded, and the portion of the braided implant 300 that does not invert to form the occlusive sack 308 can be pushed into the occlusive sack 308 forming an embolic filler braid 310. As shown, the embolic filler braid 310 can remain attached to the inner elongated member 400 by a braid release mechanism 404. While the embolic filler braid 310 is attached to the inner elongated member 400, the braided implant 300 can be partially or fully retracted by pulling the inner elongated member 400 proximally. Once retracted, the implantation system can be repositioned and the inner elongated member 400 can be pushed distally to re-implant the braided implant 300.

Figure 5E:
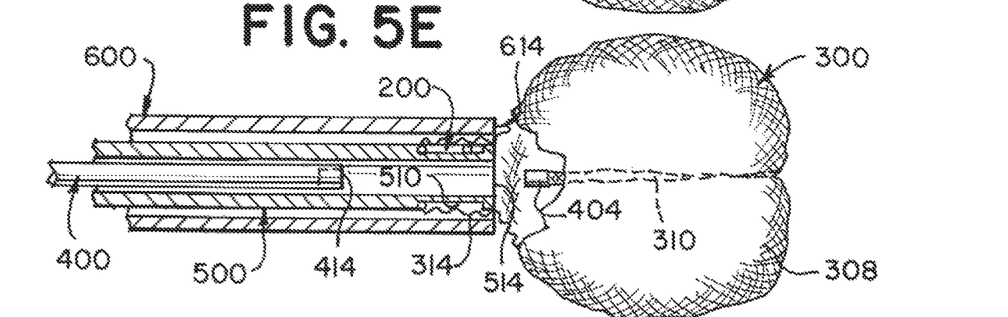

As shown in FIG. 5E, the braided implant 300 can be released from the inner elongated member 400 by detaching the braid release mechanism 404.

Figure 5F:
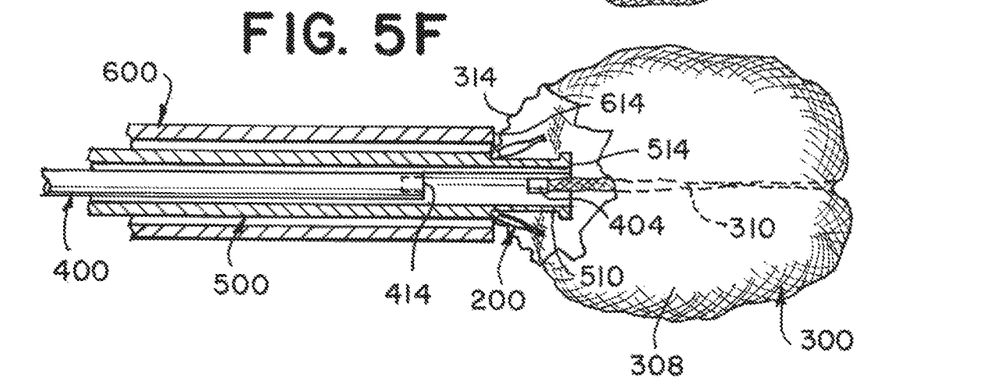

As shown in FIG. 5F, the delivery tube 500 can be pushed distally from the microcatheter 600, or the microcatheter 600 can be pulled proximally, and the expansion ring 200 can begin to expand from a delivery configuration as shown in FIGS. 5A to 5E to an expanded configuration. As the expansion ring 200 expands, it can begin to disengage the notch 510 in the delivery tube 500. The expansion ring 200 can be made of a memory shape material that has a deformed shape in the delivery configuration that is crimped to fit within the notch 510 in the delivery tube and a predetermined shape that the expansion ring 200 expands to in the expanded or deployed configuration. When the delivery tube 500 exits the microcatheter 600, the expansion ring 200 can make contact with bodily fluids, and the temperature of the bodily fluids can cause the expansion ring 200 to expand to the predetermined shape.

Figure 5G:
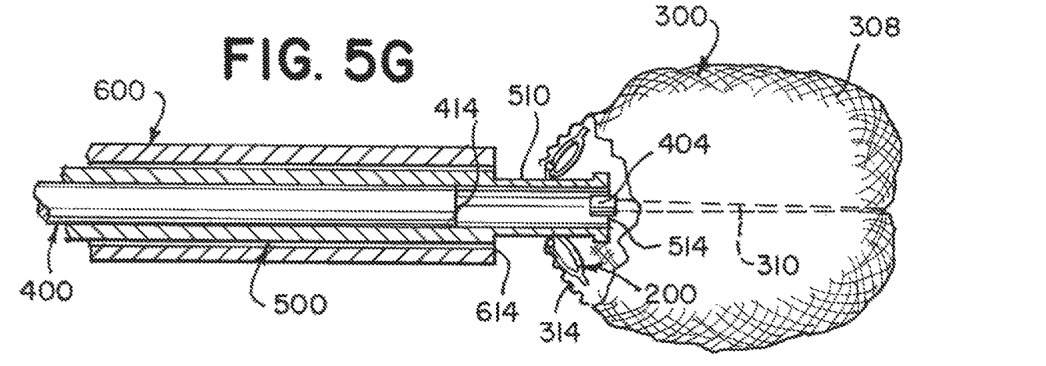

As shown in FIG. 5G, the expansion ring 200 can continue to expand and disengage from the notch 510 in the delivery tube 500. Once the expansion ring 200 is fully expanded in the deployed configuration, the delivery tube can be extracted.

Figure 6:
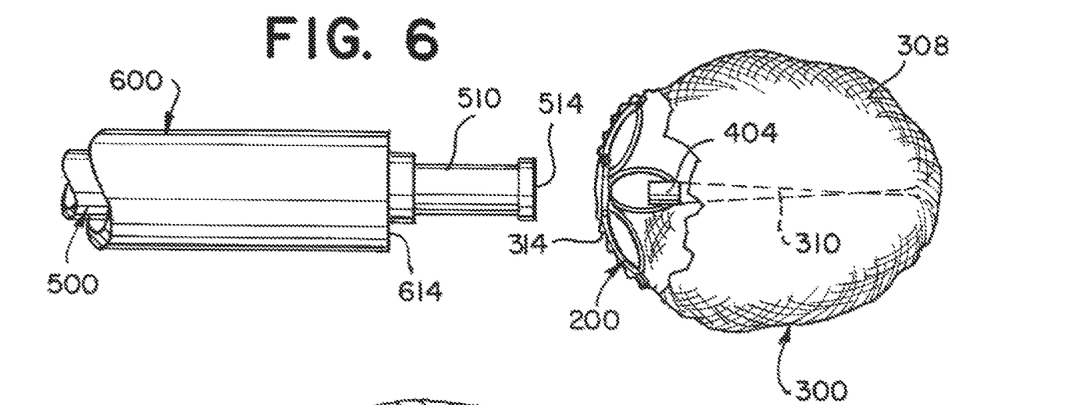
FIG. 6 is a drawing depicting a braided implant in an implanted configuration with an expansion ring in a deployed configuration according to the present invention.

FIG. 6 depicts a braided implant in an implanted configuration with an expansion ring in a deployed configuration. The delivery tube 500 and microcatheter 600 can be extracted from the patent.

Figure 7A:
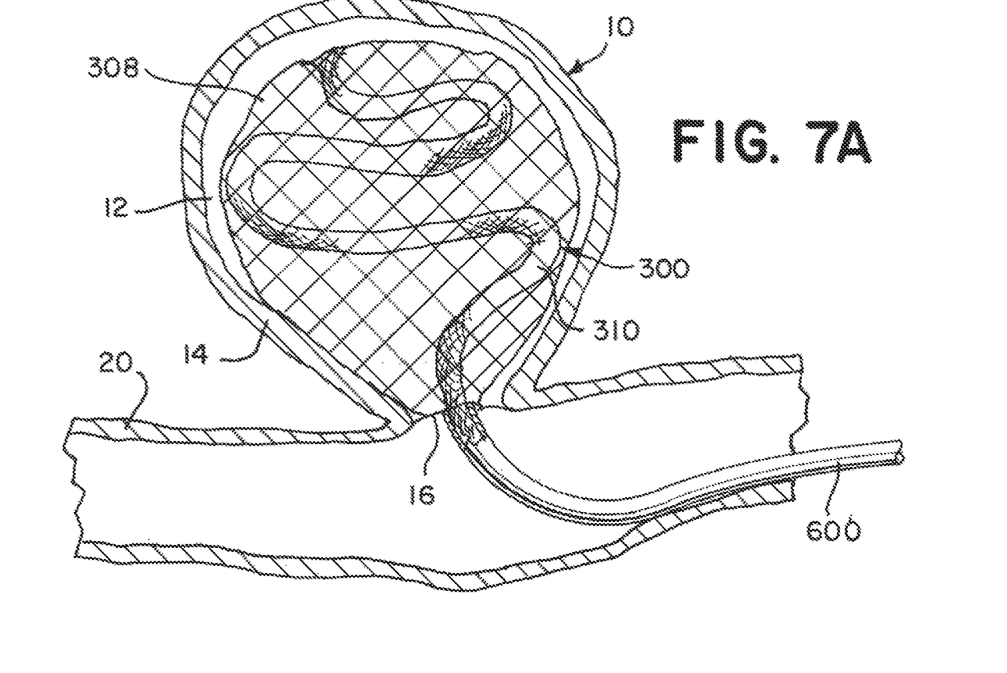
FIG. 7A is a cut-away drawing of an aneurysm with a partially implanted braided implant.

FIG. 7A depicts a cut-away of an aneurysm 10 with a partially implanted braided implant 300. A delivery catheter 600 can be delivered through a blood vessel 20 to a neck 16 of the aneurysm, and the braided implant 300 can be pushed through the neck 16 into the aneurysm 10 to form an occlusive sack 308 that extends to walls of the aneurysm 10. The partially implanted braided implant 300 can be retracted and repositioned.

Figure 7B:
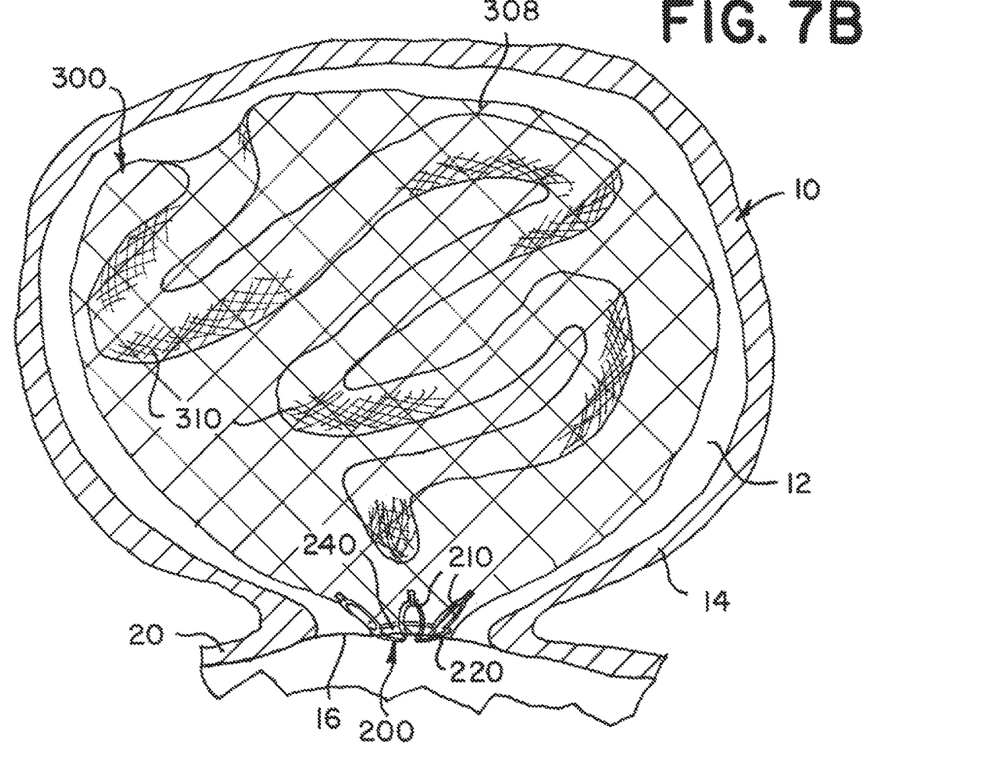
FIG. 7B is a cut-away drawing of an aneurysm with a completely implanted braided implant.

FIG. 7B depicts a cut-away of an aneurysm 10 with a completely implanted braided implant 300. An occlusive sack 308 extends the walls 14 of the aneurysm 10, and an embolic braid 310 can fill the occlusive sack 308. Together, the occlusive sack 308 and embolic braid 310 can fill the aneurysm sac 12. The expansion ring 200 can reside near the aneurysm neck 16 and can have extending portions 210 that extend to appose the occlusive sack 308. The expansion ring 200 can have attaching segments 220 that connect the extending portions 210, and the attaching segments 220 can form a ring or other shape that defines an opening 240 of the expansion ring 200 and occlusive sack 308.

Figure 8A:
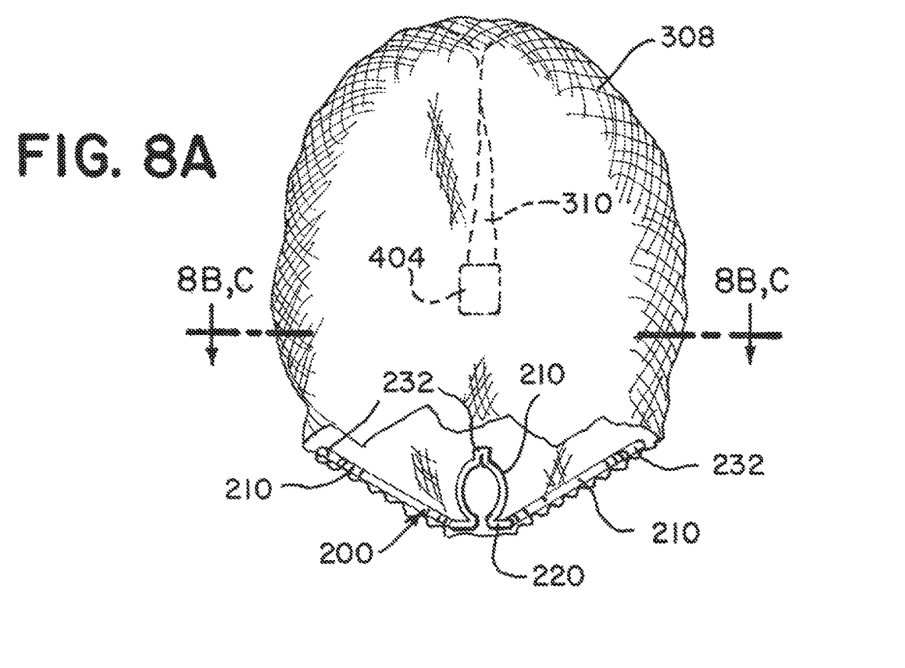
FIGS. 8A to 8C is drawing depicting a braided implant in an implanted configuration and an expansion ring in a deployed configuration according to the present invention.
Figures 8B, 8C, 9A, 9B:
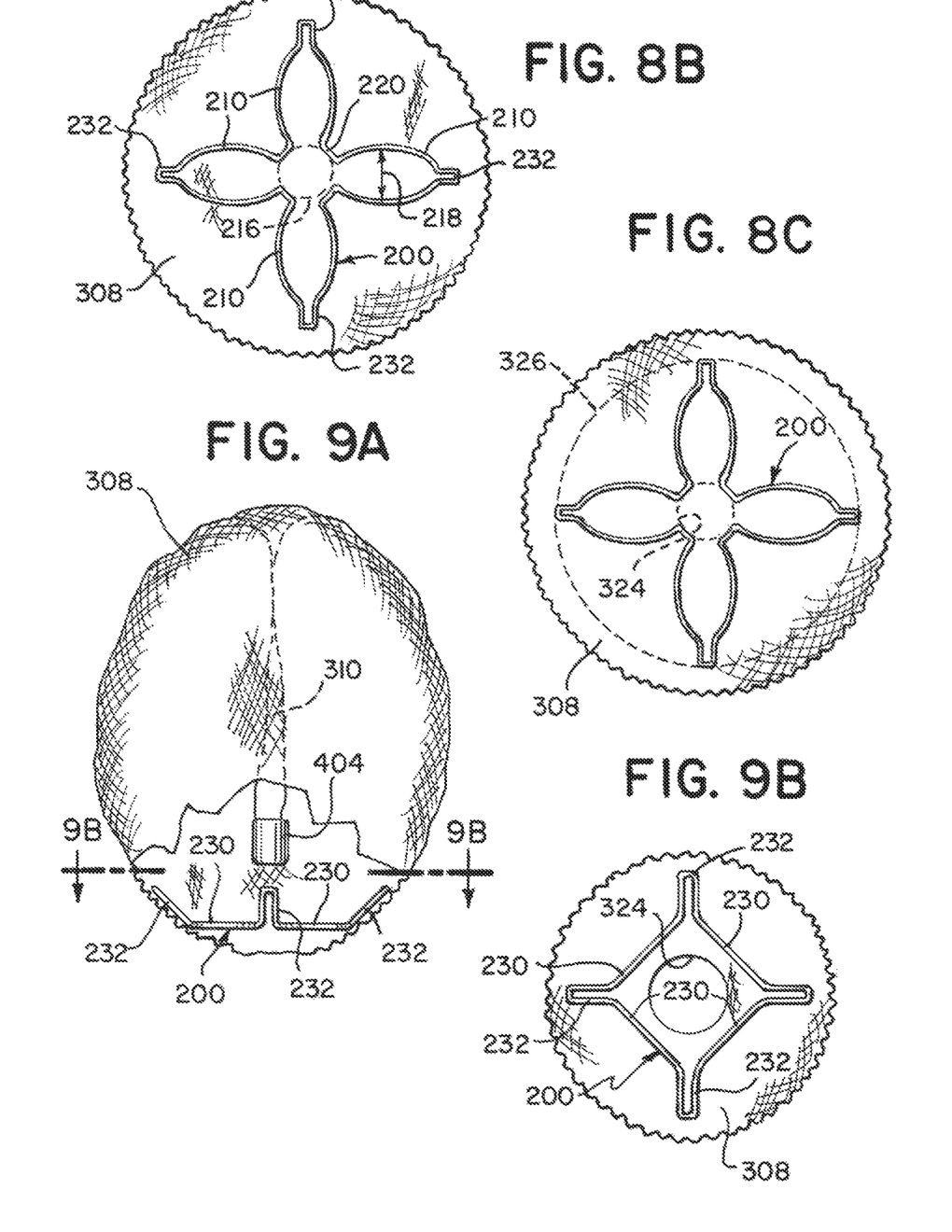
FIGS. 9A to 9B is a drawing depicting a braided implant in an implanted configuration and an expansion ring in a deployed configuration according to the present invention.

FIGS. 8A to 8C depict a braided implant 300 in an implanted configuration and an expansion ring 200 in a deployed configuration. As shown in FIGS. 8A to 8C, the expansion ring 200 can have leaf or petal shaped extending portions 210 connected by attaching segments 220. The expansion ring 200 can have a collapsed configuration as shown in FIG. 2B and expand to a deployed configuration as shown in FIGS. 8A to 8C. FIG. 8A depicts a side view of an occlusive sack 308 having an embolic filler braid 310 and the expansion ring 200. FIGS. 8B and 8C illustrate a cross-sectional view of the occlusive sack 308 as indicated in FIG. 8A. Referring to FIG. 8B, the expansion ring can be constructed with multiple independent sections that are connected together with segment connectors 232. As shown, each extending portion 210 can have a connector 232 positioned to connect two halves of each extending portion 210. The occlusive sack 308 can be connected to the expansion ring at the attaching segments 220, and the extending portions can be free to slide against the occlusive sack 308 as the expansion ring 200 opens to the deployed configuration. As illustrated in FIG. 8C, the attaching segments 220 can define a first circumference 324 of the occlusive sack 308 near an opening in the occlusive sack 308, and the extending portions 210 can open the occlusive sack to a larger, second circumference 326.

FIGS. 9A and 9B depict a braided implant 300 in an implanted configuration and an expansion ring 300 in a deployed configuration. FIG. 9A is a side view, and FIG. 9B is a cross-sectional view as indicated in FIG. 9A. As shown in FIGS. 9A and 9B, the expansion ring 200 can have four segments 230 connected by connectors 232 to form four corners.

Figure 10A:
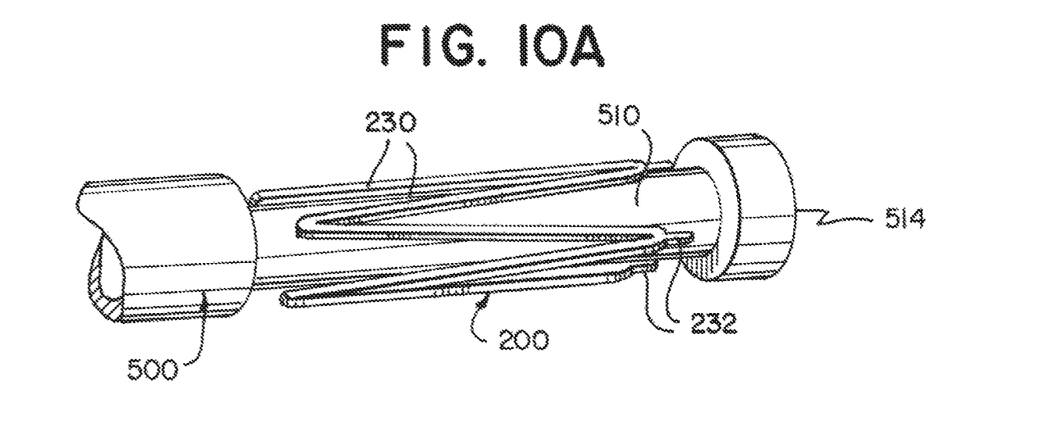
FIGS. 10A, and 10B are drawings depicting expansion rings in a collapsed configuration according to the present invention.
Figure 10B:
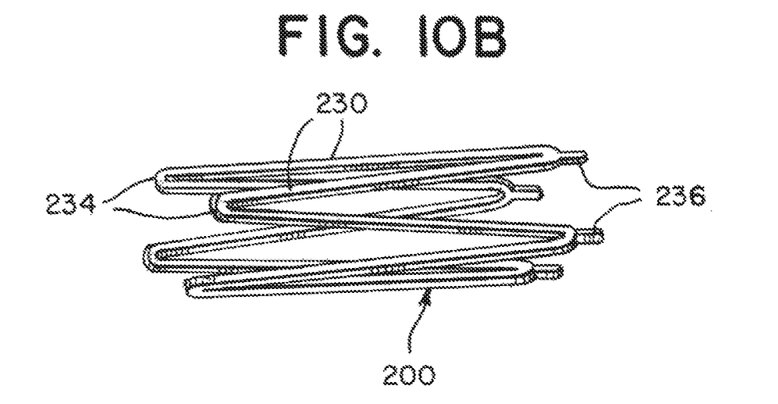

FIGS. 10A and 10B depict an expansion ring 200 in a collapsed configuration. The expansion ring 200 can be shaped as shown in FIGS. 10A and 10B in the collapsed configuration and expand to a deployed configuration. FIG. 10A depicts the expansion ring 200 within a notch 510 of a delivery tube, and FIG. 10B depicts the expansion ring of FIG. 10A absent the delivery tube. As shown, the segments 230 can be substantially straight, and bends 234 or connectors (not shown) can join the segments 230 to form a zig zag structure. The expansion ring can include attachment tabs 236 for attaching to a braided implant 300.

As will be appreciated and understood, an expansion ring can have any number of segments, bends, and connectors to form a zig-zag shape. In a collapsed configuration, the zig-zag shape can have a tubular shape, having a substantially uniform circumference along its length. In an expanded or deployed configuration, the expansion ring can have a tubular shape having a substantially uniform circumference larger than the collapsed circumference or a tapered shape having a first circumference near the occlusive sack opening and a second circumference at a region within an occlusive sack that is larger than the first circumference.

Figure 11:
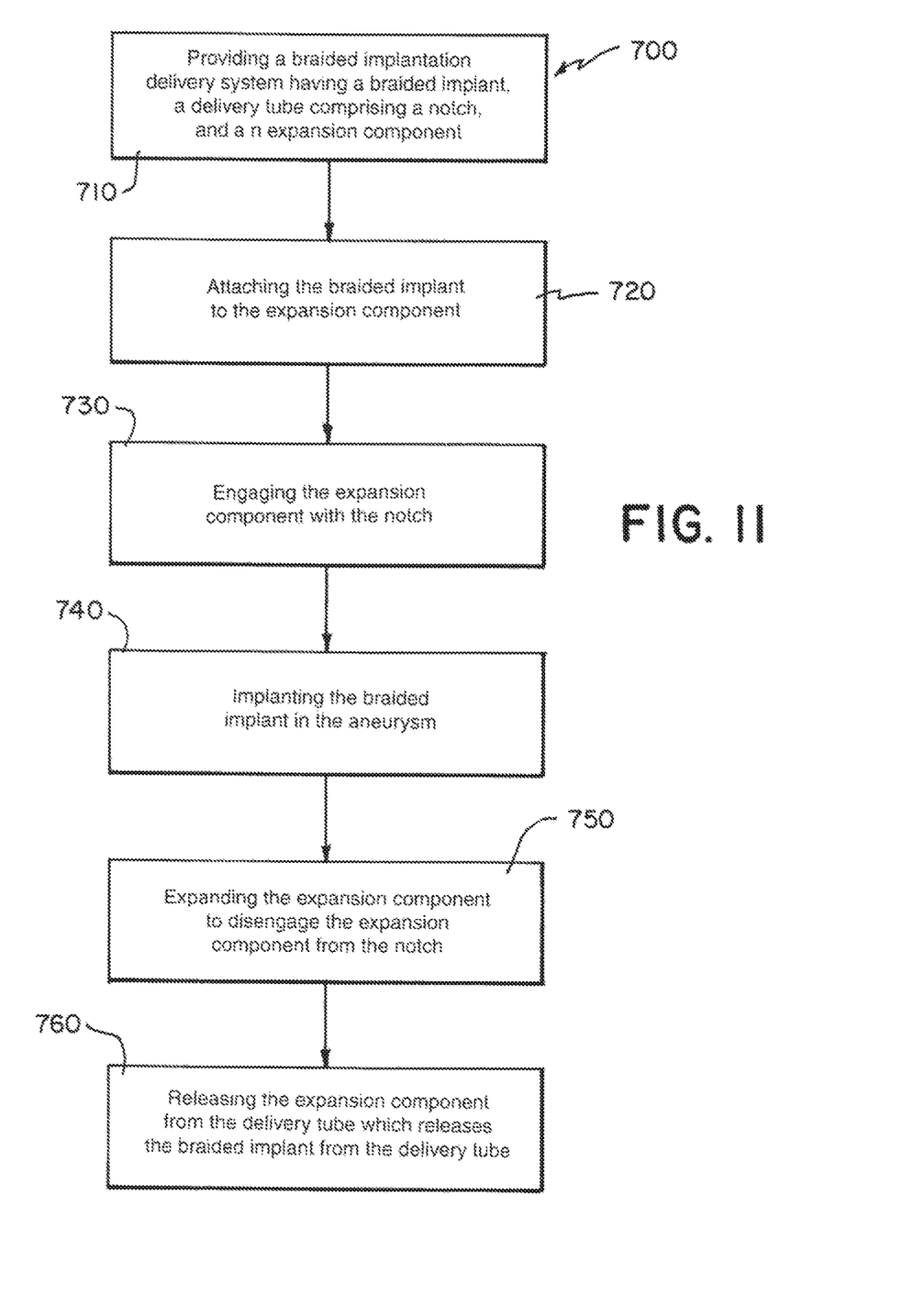
FIGS. 11 and 12 are flow diagrams outlining method steps according to the present invention.
Figure 12:
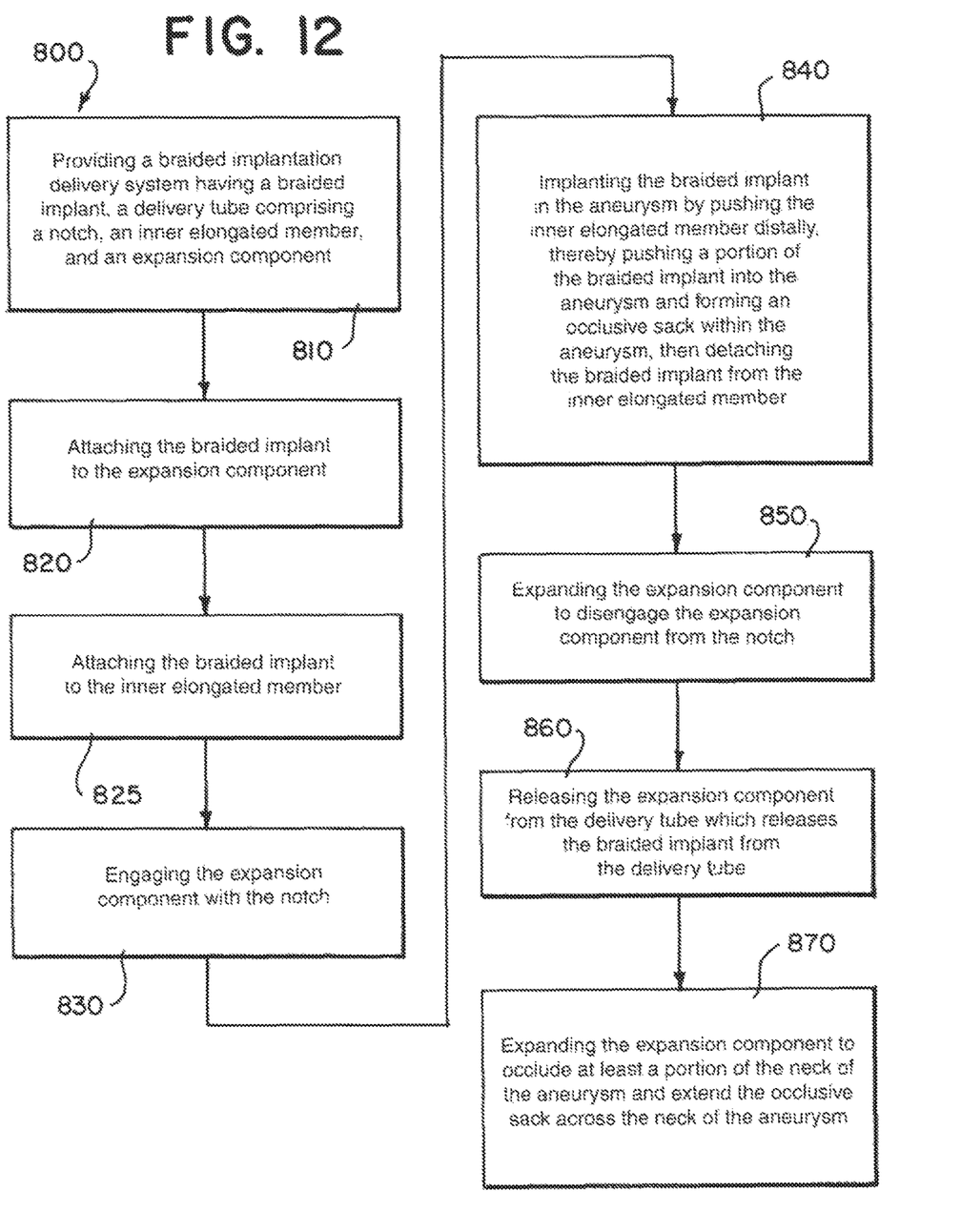

Expansion rings disclosed herein are preferably formed of a shape memory material such as nickel-titanium alloy, or a shape memory polymer, for example, having a shape memory position in an expanded configuration. The expansion rings can be appropriately heat treated so that the expansion ring forms in the desired shape of the expanded shape memory position. Each expansion ring can be formed by cutting a tube or a sheet formed of a shape memory material such as nickel-titanium alloy, or shape memory polymer, by a laser FIGS. 11 and 12 are flow diagrams outlining example method steps for use of a device or system for treating an aneurysm. The method steps can be implemented by any of the example means described herein or by any means that would be known to one of ordinary skill in the art.

Referring to method 700 outlined in FIG. 11, in step 710, a braided implantation delivery system having a braided implant, a delivery tube, and an expansion component can be provided. In step 720, the braided implant can be attached to the expansion component. In step 730, the expansion component can be engaged with a notch on the delivery tube. In step 740, the braided implant can be implanted into the aneurysm. In step 750, the expansion component can be expanded to disengage the expansion component from the notch. In step 760, the expansion component can be released from the delivery tube, thereby releasing the braided implant from the delivery tube.

Referring to method 800 outlined in FIG. 12, in step 810, a braided implantation delivery system having a braided implant, a delivery tube, an inner elongated member, and an expansion component can be provided. In step 820, the braided implant can be attached to the expansion component. In step 825, the braided implant can be attached to the inner elongated member. In step 830, the expansion component can engage a notch on the delivery tube. In step 840, the braided implant can be implanted into the aneurysm by pushing the inner elongated member distally, thereby pushing a portion of the braided implant into the aneurysm and forming an occlusive sack within the aneurysm, then detaching the braided implant from the inner elongated member. In step 850, the expansion component can be expanded to disengage the expansion component from the notch. In step 860, the expansion component can release the delivery tube, thereby releasing the braided implant from the delivery tube. In step 870, the expansion component can expand to occlude at least a portion of the neck of the aneurysm and extend the occlusive sack across the neck of the aneurysm.

The descriptions contained herein are examples of embodiments of the invention and are not intended to limit the scope of the invention. As described herein, the invention contemplates many variations and modifications of a system, device, or method that can be used to treat an aneurysm with a braided implant. Variations can include but are not limited to alternative geometries of elements and components described herein, utilizing any of numerous materials for each component or element (e.g. radiopaque materials, memory shape metals, etc.), utilizing additional components including components to position the braided implant at a treatment site, extract the braided implant, or eject a portion of the braided implant from the interior of the delivery tube, utilizing additional components to perform functions described herein, or utilizing additional components to perform functions not described herein, for example. These modifications would be apparent to those having ordinary skill in the art to which this invention relates and are intended to be within the scope of the claims which follow.

The invention claimed is:

1. A system for releasing an implant, the system comprising:
 a braided implant comprising a first end and a second end;
 a delivery tube comprising a distal end and an outer surface comprising a notch thereon approximate the distal end;
 an inner elongated member comprising a distal end detachably attached to the first end of the braided implant; and
 an expansion ring mechanically connected to the braided implant near the second end of the braided implant and movable from a collapsed configuration to a deployed configuration, the collapsed configuration engaging with the notch, and the deployed configuration disengaging the notch, thereby releasing the delivery tube.

2. The system of claim 1 wherein the braided implant comprises:
 a fold positioned distal the distal end of the delivery tube,
 an outer fold segment extending proximally from the fold and comprising the second end of the braided implant, and
 an inner fold segment encompassed by the outer fold segment, extending proximally from the fold, and comprising the first end of the braided implant.

3. The system of claim 2 wherein the expansion ring is mechanically connected to a portion of the outer fold segment, the outer fold segment covering at least a portion of the notch and at least a portion of the expansion ring.

4. The system of claim 2 wherein the delivery tube further comprises a lumen therethrough and the inner fold segment of the braided implant is positioned within the lumen.

5. The system of claim 1 wherein the deployed configuration of the expansion ring comprises:
 an attaching segment attached to the braided implant and opening a first region of an occlusive sack of the braided implant to a first circumference; and
 an extending portion attached to the attaching segment and opening a second region of the occlusive sack to a second circumference greater than the first circumference.

6. The system of claim 1 wherein the expansion ring comprises a plurality of leaf shaped elements that extend radially as the expansion ring moves from the collapsed configuration to the deployed configuration.

7. The system of claim 1 wherein the expansion ring in the collapsed configuration comprises a plurality of segments joined to form a substantially tubular zig-zag structure.

8. The system of claim 1 wherein pushing the inner elongated member distally pushes the braided implant distally to implant at least a portion of the braided implant.

9. A device for treating an aneurysm, the device comprising:
 a tubular delivery member comprising a distal end, an interior, an exterior, and a notch positioned on the exterior approximate the distal end;
 an inner elongated member positioned within the interior of the tubular delivery member comprising a distal end and a proximal end;
 a braided tubular implant movable from a delivery configuration to an implanted configuration, the delivery configuration comprising:
  a first end extending proximally within the interior of the tubular delivery member and detachably attached to the distal end of the inner elongated member, and
  a second end extending distally from the distal end of the tubular delivery member and folding proximally over at least a portion of the notch; and
 an expansion component positioned within the notch and attached to the braided tubular implant approximate the second end, the expansion component movable from a collapsed configuration to a deployed configuration, the collapsed configuration engaging the notch and the deployed configuration disengaging the notch.

10. The device of claim 9 wherein the notch comprises a circumferential indentation on the exterior of the tubular delivery member.

11. The device of claim 10 wherein the expansion component is positioned in the circumferential indentation when in the collapsed configuration.

12. The device of claim 9 wherein the implanted configuration of the braided tubular implant comprises an occlusive sack, and wherein the expansion component is positioned within the occlusive sack.

13. The device of claim 12 wherein the expansion component comprises a plurality of extending members apposing the occlusive sack in the deployed configuration.

14. The device of claim 9 wherein the collapsed configuration of the expansion component comprises an opening through which the braided tubular implant passes through upon movement from the delivery configuration to the implanted configuration.

* * * * *